United States Patent [19]

Shaw et al.

[11] Patent Number: 5,457,223

[45] Date of Patent: * Oct. 10, 1995

[54] PROCESS FOR ELIMINATION OF WASTE MATERIAL DURING MANUFACTURE OF ACRYLONITRILE

[75] Inventors: Wilfrid G. Shaw, Lyndhurst; Kenneth L. Bigler, Aurora; Louis R. Trott, Solon; Steve J. Miko, Hudson; Vincent G. Reiling, Shaker Heights; Michael J. Seely, Twinsburg; Dev D. Suresh, Hudson; Maria S. Friedrich, Lyndhurst, all of Ohio; Paul E. Bott, Victoria; Edward J. Sockell, Port Lavaca, both of Tex.; Albert R. Shuki, Jr., Sagamore Hills, Ohio; Kenneth P. Keckler, Lima, Ohio; Frank J. Kocjancic, Independence, Ohio; Steven J. Rowe, Medina, Ohio

[73] Assignee: The Standard Oil Company, Cleveland, Ohio

[ * ] Notice: The portion of the term of this patent subsequent to Feb. 22, 2011 has been disclaimed.

[21] Appl. No.: 104,752

[22] Filed: Aug. 11, 1993

Related U.S. Application Data

[63] Continuation-in-part of Ser. No. 959,237, Oct. 9, 1992, Pat. No. 5,288,473.
[51] Int. Cl.⁶ .......................... C07C 253/32; C07C 253/34
[52] U.S. Cl. .......................... 558/319; 423/237; 558/320
[58] Field of Search ...................................... 558/319, 320

[56] References Cited

U.S. PATENT DOCUMENTS 3,911,089  10/1975  Shiraishi et al. .................. 423/376
5,288,473  2/1994  Shaw et al. ........................ 558/319

OTHER PUBLICATIONS

Patent Application No. 1978–35,232 (Japan), Oct. 2, 1979.
Patent Application No. 1974–87,474 (Japan),–5–1–016615, Apr. 17, 1979.
Derwent World Patent Index JP 51–16615. (Date not available).

*Primary Examiner*—Joseph Paul Brust
*Attorney, Agent, or Firm*—Michael F. Esposito; David J. Untener

[57] ABSTRACT

A process for the substantial or complete elimination of ammonium sulfate generated during the production of acrylonitrile by the direct ammoxidation of propylene/propane, ammonia and an oxygen containing gas (e.g. air) over a fluid bed catalyst wherein the improvement comprises introducing methanol into said reactor in the upper portion of the reactor at a location where the methanol reacts with at least a portion if not substantially all of the excess ammonia without affecting the acrylonitrile yield. Preferably, methanol is introduced into the reactor at below its coking temperature. In particular, when an oxygen lean fluid bed catalyst is utilized, an additional oxygen containing gas is introduced into the reaction at a distance between about 8 to 14 inches from the methanol feed location.

31 Claims, No Drawings

5,457,223

PROCESS FOR ELIMINATION OF WASTE MATERIAL DURING MANUFACTURE OF ACRYLONITRILE

RELATED APPLICATION

This application is a continuation-in-part of U.S. Ser. No. 07/959,237 filed Oct. 9, 1992, now U.S. Pat. No. 5,288,473.

BACKGROUND OF THE INVENTION

The present invention is directed to substantial elimination of unreacted ammonia and the dramatic reduction in ammonium sulfate and resulting waste products produced from the unreacted ammonia during the manufacture of acrylonitrile by the direct ammoxidation of an unsaturated or saturated hydrocarbon, preferably propylene or propane, ammonia and oxygen in a fluid bed reactor containing an ammoxidation catalyst. In particular, the present invention is directed to the addition of oxygen containing compound, preferably methanol, at a specific location in the fluidized bed reactor during the manufacture of acrylonitrile to reduce substantially or eliminate the amount of ammonia remaining in the gaseous effluents exiting the fluidized bed reactor which translates into a complete or substantial reduction of the production of ammonium sulfate during the recovery and purification of the acrylonitrile so produced. This substantial reduction or complete elimination in the generation of ammonium sulfate during the practice of the manufacture of acrylonitrile leads to significant environmental and economic advantages.

There are several patents which address the issue of the injection of methanol into a fluid bed reactor to produce hydrogen cyanide. In addition, these references further disclose the injection of methanol into an acrylonitrile fluid bed reactor to produce hydrogen cyanide while manufacturing acrylonitrile. For example, U.S. Pat. Nos. 3,911,089 and 4,485,079 each teach the ammoxidation of methanol to produce hydrogen cyanide by injection of methanol into a fluid bed reactor containing an ammoxidation catalyst suitable for the manufacture of acrylonitrile. In addition, each of these references teach that the methanol injection can be made simultaneously with the manufacture of acrylonitrile. Moreover, Japanese Patent Applications 74-87,474, 79-08655 and 78-35232 all are related to similar methods of increasing or making hydrogen cyanide during the manufacture of acrylonitrile. Japanese patent application 74-87,874 also suggests that a secondary effect of their procedure is the decrease of the amount of unreacted ammonia with a resulting decrease in the amount of sulfuric acid used for neutralization. All of these patents are primarily concerned with the production of additional hydrogen cyanide.

The present invention is directed to a specific procedure for injection of an oxygenate compound(s) or mixture or organic materials capable of reacting with ammonia, preferably methanol, into the fluid bed reactor at a specific location and direction to obtain substantial or complete elimination of the production of ammonium sulfate produced during the manufacture, recovery and purification of the acrylonitrile without any decrease in the acrylonitrile production.

SUMMARY OF THE INVENTION

It is a primary object of the present invention to eliminate or substantially reduce the amount of ammonium sulfate generated during the manufacture of acrylonitrile.

It is a further object of the present invention to eliminate or substantially reduce the amount of unreacted ammonia exiting the reactor effluents during the manufacture of acrylonitrile.

Additional objects, advantages and novel features of the invention will be set forth in part in the description which follows, and in part will become apparent to those skilled in the art upon examination of the following or may be learned by practice of the invention. The objects and advantages of the invention may be realized and obtained by means of the instrumentalities and combinations particularly pointed out in the appended claims.

To achieve the foregoing objects in accordance with the purpose of the present invention as embodied and described herein, the method of the present invention comprises introducing into the lower portion of a fluid bed reactor a hydrocarbon selected from the group consisting of propylene and propane, ammonia and oxygen containing gas to react in the presence of a fluid bed catalyst to produce acrylonitrile, introducing an oxygen containing compound capable of reacting with ammonia into the fluid bed reactor at a point where the oxygen containing compound does not substantially affect the reaction of the hydrocarbon, ammonia and oxygen containing gas to produce acrylonitrile and reacts with substantially all the unreacted ammonia present in the reactor to substantially eliminate the presence of any free ammonia in the reactor effluent exiting said reactor, passing the reactor effluent containing acrylonitrile and substantially free of any unreacted ammonia into a quench column to cool the reactor effluent with water in the absence of sulfuric acid to remove unwanted impurities and recovering the acrylonitrile from the quench column.

In a preferred embodiment of the process of the present invention the oxygenate compound is selected from the group consisting of formaldehyde and methanol or mixtures thereof, most preferably methanol.

In another preferred embodiment of the process of the present invention the oxygenate compound, preferably methanol, is introduced into the reactor at a temperature below its coking temperature (about 680°– 700° F.).

In still another preferred embodiment of the process of the present invention the methanol is injected into the reactor through a conduit which is capable of maintaining the temperature of the methanol below its coking temperature prior to exit into the reactor. Preferably, the conduit comprises an insulated sparger comprising at least one header pipe connected to at least one lateral tube containing at least one nozzle and/or alonized, ceramic or coated sparger.

In a further preferred embodiment of the process of the present invention the point of injection of the methanol into the reactor is above the point of introduction of the propylene, ammonia and oxygen containing gas (e.g. air), preferably above at least 70% of the calculated expanded bed height, most preferably above 85%, especially preferred being above 90%.

In a still further preferred embodiment of the process of the present invention the methanol is injected into the reactor in an upward direction.

In another aspect of the present invention as embodied and broadly described herein, the method of the present invention comprises introducing a hydrocarbon selected from the group consisting of propylene and propane, ammonia and an oxygen containing gas into the lower portion of a fluid bed reactor containing a fluid bed ammoxidation catalyst to react in the presence of said catalyst to produce acrylonitrile wherein the improvement comprises introducing an oxygenate compound capable of reacting with ammonia in an upward direction into the upper portion of the fluid bed reactor at a point where the oxygenate does not substantially affect the reaction of the hydrocarbon, ammonia and oxygen containing gas to produce acrylonitrile and reacts with substantially all of the unreacted ammonia present in the reactor to substantially eliminate ammonia from the reactor effluents exiting the reactor.

In a preferred embodiment of the present invention the methanol is injected into the upper portion of the reactor at a location above at least 70 percent of the calculated expanded fluid catalytic bed height.

In a still further preferred embodiment of the present invention the methanol is injected into the upper portion of the fluid bed reactor at a location above at least 85 percent of the calculated expanded fluid catalytic bed height.

In a still further preferred embodiment of the present invention the methanol is injected into the upper portion of the fluid bed reactor at a location above at least 90 percent of the calculated expanded fluid catalytic bed height.

In another preferred embodiment of the present invention the methanol is injected into the fluid bed reactor via a conduit which is capable of maintaining the temperature of the methanol below its coking temperature prior to exit into the reactor.

In a still preferred embodiment of the present invention the conduit means for the methanol comprises a sparger comprising at least one header pipe connected to at least one lateral tube containing at least one nozzle.

In still another preferred embodiment of the present invention the inside of the conduit for said methanol is maintained at a temperature below the coking temperature of the methanol by providing a blanket of thermal insulation about the outer surface of the conduit. Preferably, a second conduit is provided about the outside surface of the thermal insulation to further provide a protective surface for said thermal insulation.

Typical oxygenate compounds which may be suitable in the practice of the present invention are aldehydes, carboxylic acids, ketones, alcohols, esters or mixtures thereof. The mandatory requirement of the oxygenate compound is that it react with any excess ammonia in the reactor to substantially eliminate free ammonia from exiting the reactor and not compete with the efficiency of the primary reaction to produce acrylonitrile. The preferred oxygenate compounds are formaldehyde and methanol, especially preferred being methanol.

In a still further preferred embodiment of the process of the present invention a mixture of organic compounds having at least one compound capable of reacting with substantially all of the excess ammonia in the reactor but not effecting the efficiency of the primary reaction to produce acrylonitrile is introduced into the reactor. Illustrative of such mixtures may be organic or aqueous waste stream containing olefinic compounds, substituted aromatics and/or oxygenates.

The significance of the process in the present invention is that it provides a simple and economic procedure for the substantial elimination of ammonia breakthrough (i.e. unreacted $NH_3$) in a fluid bed reactor along with the attendant advantage of eliminating ammonium sulfate as a by-product during the manufacture of acrylonitrile. The elimination of ammonium sulfate from the waste stream during acrylonitrile manufacture means that the waste stream does not contain any or only a minimal amount of inorganic salt. This leads to significant economic advantages in the practice of the acrylonitrile process if one cannot practice deepwell injection. Currently, the waste stream emanating from the quench column contains $(NH_4)_2SO_4$ in a fairly high concentration which makes the disposal of these streams in an economic and environmental acceptable manner difficult. The elimination or minimization of this ammonium salt from this stream can make these streams acceptable to treatment by waste treatment procedures which do not require severe conditions or expensive materials of construction (e.g. incineration), or if deepwell injection isn't available leading to significant economic and environmental advantages.

Reference will now be made in detail to the present preferred embodiment of the invention.

DETAILED DESCRIPTION OF THE INVENTION

The present invention minimizes the production of ammonium sulfate generated during the manufacture of acrylonitrile by adding an oxygenate compound(s) or a mixture of organic compounds having at least one compound capable of reacting with ammonia, preferably methanol to the fluid bed reactor at a location which allows for the substantial or complete reaction of excess ammonia in the reactor with the oxygenate compound without substantially affecting the efficiency of the acrylonitrile production. The substantial elimination or complete elimination of ammonium sulfate from the waste stream emanating from the quench column of an acrylonitrile plant dramatically improves the environmental impact and economics associated with the practice of the acrylonitrile process.

In the preferred practice of the present invention, methanol is injected into the fluid bed reactor in the catalyst zone or above (i.e. a height above 100% of the expanded catalyst bed height) from a sparger at a position where it will have an opportunity to react with substantially all or all of the excess ammonia but not be competitive with the main propylene ammoxidation reaction occurring in the lower portion of the catalyst bed. For the purposes of the present invention, the term fluid bed reactor is intended to not only encompass conventional fluid bed reactors but also any reactor capable of maintaining the catalyst in a fluid state such as transport line reactors, riser reactors or recycle reactors.

In another preferred embodiment of the present invention the location of the methanol feed should be at a level calculated at 70 percent of the level of the expanded catalyst bed height, preferably 80 to 90 percent of the expanded catalyst bed height, most preferably being over 90 percent of expanded catalyst bed height. The term expanded catalyst bed height as used in this application means the catalyst bed height while the catalyst is in the fluidized bed state. That is, the bed height when the gaseous components are present in the fluidized bed reactor and mixing with catalyst.

The oxygenate (preferably methanol) can be injected neat, or in the presence of other gases such as nitrogen, steam, air, recycled off gas, etc. or combination thereof. It can be injected in liquid or vapor form by one or several means such as a sparger or sprayer in any direction, preferably, in an upward mode. The feed pipes can enter the reactor at the proper level, higher or lower with the proper sparger/design/direction or from a pipe from the bottom or near bottom of the usual feed grids/spargers.

The amount of methanol used can vary but should be enough to neutralize any excess ammonia breaking through into the reactor effluent. Any unreacted methanol obtained in the effluent can be recovered and recycled into the reactor or disposed by convention procedures (e.g. oxidation).

In still another preferred embodiment of the present invention, methanol is introduced into the catalyst bed at a temperature below its coking temperature (about 680°–700° F.). This is preferably accomplished by the utilization of a conventional sparger design (large header pipe, medium lateral pipes running off the header, and nozzles evenly distributed on the lateral pipes) which has been modified to prevent the temperature of the methanol from reaching its carbonization (coking) temperature before it is expelled into the catalyst bed. The sparger is modified by inclusion of a layer of insulation about the outside surface of the sparger to prevent the temperature of the inside surface of the sparger pipes/nozzles from reaching the methanol coking temperature. Most preferably the sparger is modified to include a first pipe having a second pipe disposed inside and spaced apart from the first pipe. The space between the conduits is filled with conventional thermal insulation. This design protects the insulation from abrasion of its surface by the fluidized bed catalyst.

Each propylene/propane ammoxidation catalyst operates at somewhat different feed ratios and operating conditions for maximum acrylonitrile yield and/or economic considerations. The amount of excess ammonia exiting the reactor from propylene ammoxidation reactor will vary somewhat depending on the catalyst used. The level of methanol to be added will vary according to the catalyst types and the nature of the reactor. Accordingly, in the practice of the present invention the amount of methanol injected into the reactor will be dictated by the conditions and the catalyst used. In terms of a catalyst which operates in a lean oxygen phase, it may be necessary to add additional oxygen to the reactor. However, catalyst which would operate in an excess of oxygen would not have the necessity for the addition of any oxygen to the reactor. Typically, any ammoxidation catalyst may be utilized in the practice of the present invention. For example, catalyst such as those disclosed in U.S. Pat. Nos. 3,642,930; 4,485,079; 3,911,089; 4,873,215; 4,877,764; Japanese Patent Application No. 74-87474 and 78-35232 are suitable for the practice of the present invention and are incorporated herein by reference.

As stated previously, each propylene/propane ammoxidation catalyst will operate at somewhat different feed ratios and operating conditions. During the practice of the process of the present invention the standard operating condition at which the existing propylene/propane catalyst has been operated should not have to be changed but can be changed depending upon feed and catalyst conditions. Conventional operating condition and feed ratio for the manufacture of acrylonitrile as set forth in U.S. Pat. Nos. 3,911,089 and 4,873,215 are suitable and herein incorporated by reference. However, if the catalyst utilized operates under a low or minimal oxygen environment there may be a necessity to increase the amount of oxygen into the reactor to insure that the process of the present invention operates most efficiently. This may be accomplished by increasing the oxygen ratio in the feed or actually supplying oxygen to the reactor by a separate means.

In particular, the additional oxygen added when utilizing a catalyst which operates in an oxygen lean environment should be added to the reactor via a separate sparger located adjacent to the methanol feed means. Preferably, the additional oxygen (preferably in the form of air) is injected into the reactor utilizing a convention air distribution pipe positioned about 8–14 inches below the elevated methanol insulated sparger. The oxygen/air distribution pipe may inject the additional air into the reactor in any direction. However, it is preferred that the air/distribution pipe is positioned downshot (i.e. facing downward) about 9–13 inches below the upshot methanol sparger, especially preferred being about 10–12 inches below the methanol sparger. In addition, the optimum dilute phase air ratio (moles of air/moles of MeOH) when operating with an oxygen lean ammoxidation catalyst range from greater than 0 to about 6 depending on the amount of ammonia desired to be removed from the gaseous effluents exiting the reactor. For example, the dilute phase air ratio (DPAR) for 25% reduction in ammonia will range from about greater than 0.5 to 2.0, for 50% reduction DPAR may range from 2.5 to 3.5, preferably 3, for 75% reduction DPAR will range from 3.5 to 4.5 preferably 4, and for 100% ammonia reduction the DPAR will range from 4.6 to 6.0, preferably 5 to 5.6.

For purposes of illustration only, the following examples are set forth to describe the process of the present invention.

EXAMPLE 1

A 1½ diameter reactor was charged with 550 gm of a promoted BiMoFeO propylene ammoxidation catalyst. A feed of a propylene/air/ammonia with mole ratio of 1/10.5/1.15 was passed through the catalyst bed at 443° C., 12.0 psig, at a 0.045 WWH weight hourly space velocity. After two hours on stream, propylene conversion was 98.3%, per pass conversion to AN was 76.3%, to HCN was 7.1% and about 15% of the ammonia feed breaking through. (Similar tests conducted at the same conditions at 27 hours gave 97.8%, 75.1% and 8.7%, $C_3$ conversion, AN and HCN percent, and at 42 hours gave 99.1%, 73.8%, and 8.3%, respectively, both with about 15% ammonia breakthrough).

EXAMPLE 2

The procedure of Example 1 was followed except that methanol at a mole ratio of 0.18 to 1.0 for propylene was introduced into the catalyst bed 75% from the expanded catalyst bed top. A recovery run was conducted at 75 hours on stream (total operating time), and a propylene conversion of 98.4%, ppc to AN of 72.1%, HCN of 10.1% and about a 9% ammonia feed breakthrough (down 6% from Example 1).

EXAMPLE 3

An identical test as set forth in Example 2 was followed except that the methanol was injected at 70% of the expanded bed height in an upward direction yielding 96.3% propylene, 73.3% AN, 9.4% HCN and the ammonia breaking through (in the effluent) was only 2% of the amount fed into the reactor.

EXAMPLE 4

A 1½ diameter reactor was charged with 550 grams of a promoted BiMoFeO propylene ammoxidation catalyst having a different composition than that utilized in Examples 1 to 3. Feed in a propylene/air/ammonia mole ratio of 1/9.3/1.15 was passed over the catalyst at 440° C. and 12 psig, at a weight hourly space velocity, WWH, of 0.075. After 283 hours on stream a recovery run was conducted to determine the level of products being formed; it was found that the total propylene conversion was 96.6%, per pass conversion (PPC) to acrylonitrile 78.7%, and to hydrogen cyanide 5.6%, with 5.4% of the ammonia breaking through.

EXAMPLE 5

The procedure of Example 4 was followed except that methanol at a mole ratio of 0.09 to 1.0 for propylene was introduced into the catalyst bed 30% from the top of the expanded catalyst bed in an upward direction. A recovery run was conducted at 332 hours on stream, and a total propylene conversion of 96.9%, PPC to acrylonitrile of 78.1%, HCN of 5.8% and zero percent of ammonia breaking through was found. Methanol conversion was 100%.

EXAMPLE 6

Under the same conditions of introducing feed and using the same catalyst charge as set forth in Example 5 and conducting an additional test at alternate mole ratio conditions of Propylene/air/ammonia/methanol of 1/9.3/1.08/0.09, propylene conversion was 96.1%, with PPC acrylonitrile of 77.9%, HCN of 4.9% and ammonia breakthrough of zero. Again, methanol conversion was 100%.

EXAMPLE 7

Approximately 18 tons of a propylene ammoxidation catalyst (promoted BiMoFeO) was charged to a larger acrylonitrile reactor. Feeds of propylene/air/ammonia at mole ratio of 1/10.0/1.2 were passed through the catalyst bed at 840° F., 12.0 psig. After 24 hours onstream, propylene conversion was 99.8%, per pass conversion (PPC) to AN was 75.3%, and PPC to HCN was 8.2%. Notably, 12% of the feed ammonia breaking through and sulfuric acid usage in the downstream quench operation of the process at these conditions was 0.33 gpm in order to neutralize the reactor excess ammonia. After 3 days onstream at same conditions, the catalyst gave 99.6% conversion, 75.7% PPC to AN and PPC to HCN 8.2% conversion of propylene, with about 14% of ammonia feed breaking through.

EXAMPLE 8

The same reactor was run at the same conditions as Example 7, and pure, superheated methanol vapor was injected at ca. 0.05, 0.1, 0.15, 0.2, and 0.26 mol per mole of $C_3=$, introduced into the catalyst bed at 95% of the reactor's expanded catalyst bed height. Recovery runs conducted at methanol ratios from 0 to 0.26 $MeOH/C_3=$ gave an average 99.6% propylene conversion, 76.1% per pass conversion to AN, 7.2% HCN from propylene. Total methanol conversion averaged 99.6% and per pass conversion of methanol to HCN averaged 65%. The relationship between methanol ratio, ammonia breakthrough, and sulfuric acid usage is set forth in Table 1 below:

TABLE 1

| MeOH/$C_3=$ Ratio | Sulfuric Acid (gpm) | $NH_3$B.T. (% of feed) | Acrylo (% PPC) | HCN from $C_3=$ (% PPC) | HCN from MeOH (% PPC) |
|---|---|---|---|---|---|
| 0.00 | 0.33 | 14.1 | 75.9 | 7.2 | 0 |
| 0.05 | 0.22 | 7.2 | 76.5 | 7.6 | 66.9 |
| 0.1 | 0.16 | 2.7 | 76.1 | 7.5 | 69.7 |
| 0.16 | 0.06 | 0.6 | 75.9 | 7.1 | 69.4 |
| 0.22 | 0.0 | 0.0 | 77.0 | 6.7 | 58.9 |
| 0.23 | 0.0 | 0.0 | 75.3 | 7.8 | 62.9 |
| 0.26 | 0.0 | 0.0 | 76.3 | 7.5 | 60.6 |

This demonstrates zero ammonium sulfate production (last three runs in Table 1) with no adverse effect on the normal acrylonitrile production.

EXAMPLE 9

Testing was repeated under a similar set of conditions as Example 8, except that methanol was introduced into the catalyst bed at 90% of the reactor's expanded catalyst bed height and at different ammonia feed ratios. The inventory of propylene ammoxidation catalyst was increased by about 1 ton, so that the relative position of the methanol sparget in the catalyst bed was about 90% of expanded bed height. Feeds of propylene/air/ammonia mole ratio of 1/10.0/1.1 were passed through the catalyst bed at otherwise similar conditions. At 14 days onstream, propylene conversion was 99.8%, PPC to AN was V4.4% and PPC to HCN was 8.9%. Unreacted ammonia was 8.4% of the reactor feed ammonia. The sulfuric acid usage in the downstream quench operation of the process was 0.26 gpm in order to neutralize the reactor excess ammonia. This example demonstrates that the relative position of the methanol injection point can be controlled easily by simply varying the reactor charge weight.

Methanol vapor was introduced at 90% of the reactor bed height at the above conditions. Recovery runs at 0.09 ratio of $MeOH/C_3=$ gave 99.7% total conversion, 74.8% PPC to AN, 8.0% PPC to HCN from propylene, total methanol conversion of 99.8% and PPC of methanol to HCN of 58%, reducing the ammonia breakthrough to 4.1% of feed, and reducing the sulfuric acid consumption to 0.07 gpm. Recovery runs conducted at 0.12 ratio of $MeOH/C_3=$ gave 99.7% total conversion, 74.9% PPC to AN, 7.9% PPC to HCN from propylene, total methanol conversion of 99.8% and per pass conversion of methanol to HCN of 53%, reducing the ammonia breakthrough to 0% of feed ammonia, and requiring no sulfuric acid, and forming no ammonium sulfate.

EXAMPLE 10

Repeating the testing at a similar set of conditions as in Examples 8 and 9, except that methanol was injected at 85% of the reactor's normal expanded bed height resulting in a reduction of the percentage of reactor feed ammonia breaking through from 11% to 1.8%, and subsequent lowering of ammonium sulfate generated, but also raised the selectivity of methanol to HCN while lowering the yield of AN versus introduction at 90% above of the expanded bed height.

EXAMPLE 11

In a reactor (1½ diameter) a different bismuth molybdate type ammoxidation catalyst was charged (550 grams). Feed composed of a propylene/air/ammonia mole ratio of 1/9.5/1.2 was passed through the catalyst bed at 450° C., 10 psig, at a 0.060 WWH weight hourly space velocity. Water in the form of steam at a mole ratio of 0.3 to 1.0 for propylene was introduced into the catalyst bed. Acrylonitrile conversion was 72.6%, hydrogen cyanide of 4.3% at 89.4% propylene conversion, with 6.4% of the ammonia fed breaking through.

EXAMPLE 12

The procedure of Example 11 was followed except that an aqueous (59% by volume water) stream at a mole ratio of 0.3 organics to 1.0 for propylene was introduced into the catalyst bed at 70% of the expanded bed height. It contained by mole %, 0.5 acrolein, 4.3 ethanol, 0.4 oxalic acid, 3.4 acetone, 6.9 methyl formate and 1.8 acrylic acid as well as other trace components. A recovery run was made after five hours on stream to determine the reactivities and showed a propylene conversion of 89.7%, per pass conversion to acrylonitrile of 68.2%, to hydrogen cyanide of 3.9%, and an ammonia reduction to 2.8% of that fed, breaking through. This waste stream obviously had an impact on lowering the ammonia remaining in the reactor effluent by over 50%, resulting in less neutralization required, and/or generating less ammonium sulfate, generating no additional hydrogen cyanide, and at the same time utilizing a hazardous waste by-product such as acrylic acid, and converting it to a more valuable product.

EXAMPLE 13

An identical test to Example 12 except using a non-aqueous feed, was conducted at 0.5 mole of waste organics to 1.0 mole of propylene. It contained components by mole % of 5.3 n-propanol, 3.3 isobutyl formate, 11.0 ethylene glycol, 12.8 iso-butanol, 1.5 ethyl ether, 0.6 m-xylene, 0.5 1-methyl-1-cyclohexene, and traces of other components thought capable of reaction with ammonia over a bismuth molybdate type catalyst. Analysis of the reactor effluent showed that these components were converted, in many instances to valuable products such as acrylonitrile, acetonitrile or methacrylonitrile, and a corresponding reduction in their organic waste. Dicyano benzenes were found from the m-xylene, showing that this is applicable to selected aromatics in a waste solution, as was a nitrile derivative of the olefinic substituted cyclohexene.

Example 14 set forth below illustrates the practice of the present invention where methanol is injected above the catalyst bed height.

EXAMPLE 14

Methanol at a mole ratio of 0.4 to 1.0 for propylene was introduced into the reactor above the catalyst dense phase (>100% of the expanded catalyst bed height) into the dilute zone. Comparative analysis of the products and effluent before and after the introduction of methanol showed an ammonia reduction of 15% of that breaking through prior to the use of methanol.

The above examples clearly illustrate the dramatic improvements set forth in the practice of the process of the present invention. Each of the examples shows a significant decrease in the amount of $NH_3$ breakthrough thereby substantially eliminating the amount of $(NH_4)_2SO_4$ generated without any significant impact in acrylonitrile yield. While these examples are illustrative of the practice of the present invention they are not intended to limit applicants' invention to that illustrated and obviously many modifications and variations may be utilized in light of the above teaching. It is intended that the scope of applicants' invention be defined by the claims appended hereto.

What we claim is:

1. A method for the substantial reduction of ammonia breakthrough during the manufacture of acrylonitrile comprising introducing a hydrocarbon selected from the group consisting of propane and propylene; ammonia and an oxygen containing gas into the lower portion of a fluid bed reactor containing a fluid bed ammoxidation catalyst to react in the presence of said catalyst to produce acrylonitrile wherein the improvement comprises introducing in an upward direction at least one oxygenate capable of reacting with ammonia into the upper portion of the fluid bed reactor at a point where the oxygenate does not substantially effect the reaction of the hydrocarbon, ammonia and oxygen containing gas to produce acrylonitrile and reacts with at least a portion of the unreacted ammonia present in the reactor to substantially reduce the amount of ammonia present in the reactor effluent exiting the reactor.

2. The method of claim 1 wherein the hydrocarbon is selected to be propylene.

3. The method of claim 2 wherein said oxygenate consists essentially of methanol.

4. The method of claim 1 wherein the oxygenate is injected into the upper portion of the fluid bed reactor at a location above at least 85 percent of the calculated expanded fluid catalytic bed height.

5. The method of claim 4 wherein the oxygenate is injected into the upper portion of the fluid bed reactor at a location above at least 90 percent of the calculated expanded fluid catalytic bed height.

6. The method of claim 4 wherein the oxygenate is injected into the fluid bed reactor through a conduit which maintains the temperature of the methanol below its coking temperature prior to exit into the reactor.

7. The method of claim 6 wherein the inside of the conduit for said oxygenate is maintained at a temperature below the coking temperature of the oxygenate by providing a blanket of thermal insulation about the outer surface of the conduit.

8. The method of claim 6 wherein a second conduit is provided about the outside surface of the thermal insulation to further provide a protective surface for said thermal insulation.

9. A method for the reduction of ammonia breakthrough during the manufacture of acrylonitrile comprising introducing a hydrocarbon selected from the group consisting of propane and propylene; ammonia and an oxygen containing gas into the lower portion of a fluid bed reactor containing a fluid bed ammoxidation catalyst capable of operating in an oxygen lean environment to react in the presence of said catalyst to produce acrylonitrile wherein the improvement comprises introducing into the upper portion of the fluid bed reactor (1) at least one oxygenate capable of reacting with ammonia and (2) an additional oxygen containing gas in an amount sufficient to enable said oxygenate to react with at least a portion of said ammonia at a point where the oxygenate and additional oxygen do not substantially affect the reaction of the hydrocarbon, ammonia and oxygen containing gas to produce acrylonitrile, but reacts with at least a portion of the unreacted ammonia present in the reactor to substantially reduce the amount of ammonia present in the reactor effluent exiting the reactor.

10. The process of claim 9 wherein the hydrocarbon is propylene.

11. The method of claim 10 wherein the oxygenate is injected into the upper portion of the fluid bed reactor through a conduit which maintains the temperature of the oxygenate below its coking temperature prior to exit into the reactor.

12. The method of claim 11 wherein the oxygenate is injected into the fluid bed reactor in an upward direction.

13. The process of claim 12 wherein the oxygenate consists essentially of methanol.

14. The process of claim 13 wherein the additional oxygen is added to the fluid bed reaction between the point of injection of the methanol and the point of injection for the hydrocarbon, ammonia and oxygen containing gas.

15. The process of claim 14 wherein the additional oxygen containing gas is introduced into the reactor between 8 to 14 inches from the point of introduction of the methanol.

16. The process of claim 14 wherein the additional oxygen containing gas is introduced into the reactor in a downward direction.

17. The process of claim 16 wherein the additional oxygen containing gas is introduced into the reactor at a point between 10 to 12 inches from the methanol injection.

18. The process of claim 16 wherein the mole ratio of additional oxygen containing gas per moles of methanol ranges from greater than 0 to 6.

19. The process of claim 18 wherein the oxygen containing gas is air.

20. A method for the substantial reduction of ammonia breakthrough during the manufacture of acrylonitrile comprising introducing a hydrocarbon selected from the group consisting of propane and propylene, ammonia and an oxygen containing gas into the lower portion of a fluid bed reactor containing a fluid bed ammoxidation catalyst to react in the presence of said catalyst to produce acrylonitrile wherein the improvement comprises introducing at least one oxygenate capable of reacting with ammonia below its coking temperature into the upper portion of the fluid bed reactor at a point where the oxygenate does not substantially affect the reaction of the hydrocarbon, ammonia and oxygen containing gas to produce acrylonitrile and reacts with at least a portion of the unreacted ammonia present in the reactor to substantially reduce the amount of ammonia present in the reactor effluent exiting the reactor.

21. The method of claim 20 wherein the hydrocarbon is selected to be propylene.

22. The method of claim 21 wherein said oxygenate consists essentially of methanol.

23. The method of claim 22 wherein the methanol is injected into the upper portion of the fluid bed reactor at a location above at least 85 percent of the calculated expanded fluid catalytic bed height.

24. The method of claim 23 wherein the methanol is injected into the upper portion of the fluid bed reactor at a location above at least 90 percent of the calculated expanded fluid catalytic bed height.

25. The method of claim 3 wherein the methanol is injected into the upper portion of the fluid bed reactor at a location above at least 85 percent of the calculated expanded fluid catalytic bed height.

26. The method of claim 25 wherein the methanol is injected into the fluid bed reactor through a conduit which maintains the temperature of the methanol below its coking temperature prior to exit into the reactor.

27. The method of claim 1 wherein the oxygenate is selected from the group consisting of aldehydes, carboxylic acids, ketones, alcohols, esters or mixtures thereof.

28. The method of claim 9 wherein the oxygenate is selected from the group consisting of aldehydes, ketones, carboxylic acids, alcohols, esters or mixtures thereof.

29. The method of claim 9 wherein the oxygenate reacts with at least 15 percent of the unreacted ammonia present in the upper portion of the reactor.

30. The method of claim 1 wherein the oxygenate reacts with at least 15 percent of the unreacted ammonia present in the upper portion of the reactor.

31. The method of claim 9 wherein the oxygenate reacts with at least 15 percent of the unreacted ammonia present in the reactor.

* * * * *